US009211331B2

(12) United States Patent
Smith

(10) Patent No.: US 9,211,331 B2
(45) Date of Patent: Dec. 15, 2015

(54) MINERAL BASED COMPOSITION AND METHODS OF USE

(75) Inventor: Roger Albert Alfred Smith, Sydney (AU)

(73) Assignee: TUFFROCK TECHNOLOGY PTY LIMITED, New South Wales (AU)

( * ) Notice: Subject to any disclaimer, the term of this patent is extended or adjusted under 35 U.S.C. 154(b) by 87 days.

(21) Appl. No.: 13/993,781

(22) PCT Filed: Dec. 15, 2011

(86) PCT No.: PCT/AU2011/001613
§ 371 (c)(1),
(2), (4) Date: Sep. 30, 2013

(87) PCT Pub. No.: WO2012/079121
PCT Pub. Date: Jun. 21, 2012

(65) Prior Publication Data
US 2014/0030362 A1    Jan. 30, 2014

(30) Foreign Application Priority Data

Dec. 16, 2010 (AU) ................................ 2010905512

(51) Int. Cl.
*A61K 41/00* (2006.01)
*A61K 33/06* (2006.01)
(52) U.S. Cl.
CPC .................. *A61K 41/00* (2013.01); *A61K 33/06* (2013.01); *A61K 41/0009* (2013.01)

(58) Field of Classification Search
CPC .... A61K 41/00; A61K 41/0009; A61K 33/06
See application file for complete search history.

(56) References Cited

FOREIGN PATENT DOCUMENTS

EP          1847536      * 10/2007     ........... C07D 401/06

OTHER PUBLICATIONS

TuffRock.net, About, last accessed Apr. 8, 2015, http://www.tuffrock.net/about.html, p. 1.*

* cited by examiner

*Primary Examiner* — Trevor Love
(74) *Attorney, Agent, or Firm* — Abelman, Frayne & Schwab

(57) ABSTRACT

The invention provides a process for producing a composition comprising natural alumino-silicate minerals having improved reactivity for use in methods of animal husbandry, veterinary and pharmaceutical treatment, comprising irradiating natural alumino-silicate minerals in a liquid suspension with transverse electromagnetic wave radiation in the range of 1,800 MHz to 3,000 MHz, the liquid suspension having a boiling temperature of below 120° C. The invention also provides a method of treating digestive ailments in animals comprising administering to an animal in need of same an effective amount of a composition comprising at least one natural alumina-silicate mineral which has been irradiated with transverse electromagnetic wave radiation in the range of 1,800 MHz to 3,000 MHz.

3 Claims, 12 Drawing Sheets

Average Weekly Weight Gain

Diarrhoea Index

MINERAL BASED COMPOSITION AND METHODS OF USE

TECHNICAL FIELD

The present invention relates to improvements in the processing of natural alumino-silicate minerals to produce enhanced animal husbandry, veterinary and pharmaceutical products, as well as improved methods of treatment of both human and non-human animals, and particularly mammals.

BACKGROUND ART

It is known that various natural alumino-silicate minerals are beneficial to animals, and even humans, for the treatment of a range of digestive aliments and to improve the efficiency of animal feeds. Kaolinite is widely used for the treatment of acid stomach and various digestive imbalances. Bentonite is also used for similar treatment in horses and cattle. More recently, natural and manufactured zeolites have been tested and found to have some varying degree of effectiveness in improved feed conversion, treating digestive ailments, improved animal condition and improved healing of injuries. However, the effectiveness of natural zeolites has in general been found to be rather poorer than the effectiveness of manufactured zeolites.

Natural zeolites are alumino-silicate minerals with various forms of an open box-work crystal structure. There are some 41 known natural zeolite minerals of which clinoptilolite; mordenite, erionite, chabazite and stellerite are but a small number. Molecular bonds within these crystal structures create an attractive force that pulls cations, anions and other small charged particles into the crystal structure. Some powdery natural zeolites are treated by a sintering process to improve their handling characteristics and some are dosed with metal compounds, such as manganese, to alter their reaction to various processes. In the inventor's experience, most crystalline zeolites are denigrated by excessive heat treatment. It was considered by the inventor that by using some form of irradiation it may be possible to enhance the internal molecular bonds and thereby make zeolite minerals and other natural alumino-silicate minerals more attractive to small charged particles.

It was also considered by the inventor that improving the reactivity of natural zeolites and other natural alumino-silicate minerals in this way might produce enhanced animal husbandry, veterinary and pharmaceutical products, as well as improved methods of treatment of both human and non human animals, and particularly mammals.

It was also considered by the inventor that subjecting natural alumino-silicate minerals to the type of radiation described may disturb the molecular structure of the alumino-silicate minerals and render some of the silicon atoms bioavailable.

DISCLOSURE OF INVENTION

Accordingly, in one aspect of the present invention, there is provided a method of treating digestive ailments in animals comprising administering to an animal in need of same an effective amount of a composition or product comprising at least one natural alumino-silicate mineral which has been irradiated with transverse electromagnetic wave radiation in the range of 1,800 MHz to 3,000 MHz.

According to another aspect of the present invention, there is provided a process for producing a composition or product comprising natural alumino-silicate minerals having improved reactivity for use in methods of animal husbandry, veterinary and pharmaceutical treatment, comprising irradiating natural alumino-silicate minerals in a liquid suspension with transverse electromagnetic wave radiation in the range of 1,800 MHz to 3,000 MHz, the liquid suspension having a boiling temperature of below 120° C.

According to yet another aspect of the present invention, there is provided a composition or product comprising natural alumino-silicate minerals having improved reactivity for use in methods of animal husbandry, veterinary and pharmaceutical treatment when produced by the above process.

According to yet another aspect of the present invention, there is provided a method of healing wounds in mammals comprising administering to a mammal in need of same an effective amount of a composition or product comprising at least one natural alumino-silicate mineral which has been irradiated with transverse electromagnetic wave radiation in the range of 1,800 MHz to 3,000 MHz.

Preferably, the natural alumino-silicate minerals include natural zeolite minerals.

It is preferred that the natural zeolite minerals are selected from the group consisting of clinoptilolite, mordenite, chabazite, erionite and stellerite.

In a preferred form, the liquid suspension is a water based suspension.

Preferably, the natural alumino-silicate minerals include bentonite to maintain the natural zeolite minerals in suspension.

According to one preferred form of the invention, the natural alumino-silicate minerals of the product comprise 70% w/w zeolite, 28% w/w kaolinite, and 2% w/w bentonite.

The range of zeolite in the product may be from 40% w/w to 98% w/w.

The range of kaolinite in the product may be from 0% to 58% w/w if 2% w/w bentonite is present in the product.

The range of bentonite in the product may be from 1% w/w to 50% w/w.

SUMMARY OF THE FIGURES

In order that the invention may be readily understood and put into practical effect, reference will now be made to the accompanying examples, together with photographs, in which.

DETAILED DESCRIPTION OF PREFERRED EMBODIMENTS

Experimental Work

Figure 1:
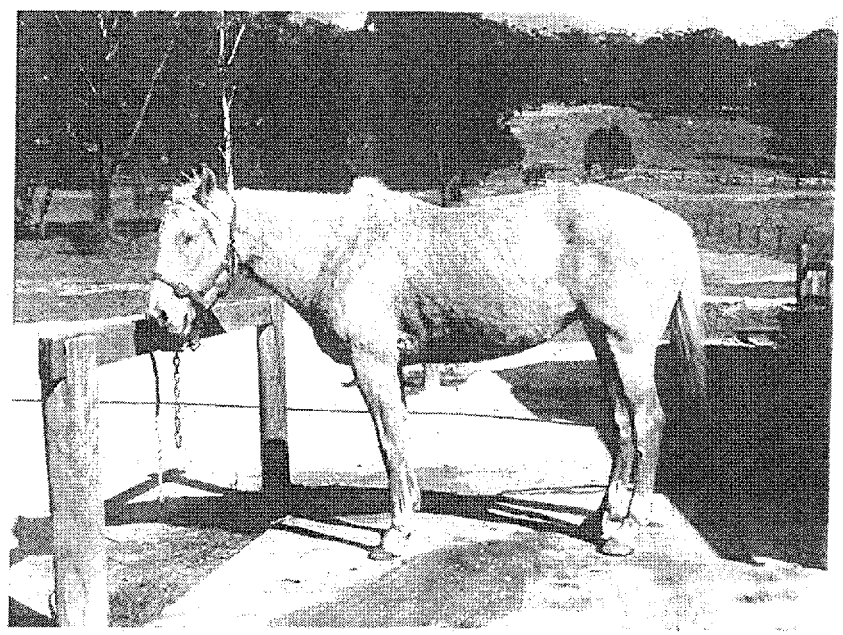
FIG. 1 is a photograph of a horse taken before the start of the trial reported in the example of Case Study 3.

In order to improve the reactivity of natural zeolite minerals and other natural alumino-silicate minerals, the application of different types of radiation was considered. These included gamma radiation, ultrasonics and transverse electromagnetic wave propagations typically in the so called microwave range. Because gamma radiation is dangerous and requires considerable infrastructure, the more readily available and safer alternative of microwave radiation was tested first. It is considered that a particular frequency of radiation, or more likely a simultaneous number of different frequencies, will be required for optimum effect. A single frequency of 2,450 MHz was however chosen for the initial tests as this would particularly react with the water of crystallisation in the minerals. Experiments showed that, whilst there seemed to be some beneficial effect, the reaction was difficult to control with a dry powder and that hotspots and local overheating occurred and could not be controlled.

The natural zeolites that were used in the experiments were from the Currabubula Formation of the Hunter Valley in New South Wales, Australia and work by the NSW Department of Mineral Resources showed that these zeolites were destroyed or at least severely denigrated by heating to more than 120° Celsius. In order to irradiate the zeolite and yet keep the generated temperature below 120° Celsius, we devised a process that will not allow the reaction to generate a temperature in excess of 120° Celsius and at the same time will allow even radiation without the development of hotspots. To achieve this we elected to irradiate the zeolite in a non-toxic liquid suspension that would not react with the zeolite and would boil at a temperature below 120° Celsius. We found a water suspension or slurry of the zeolite solids to be the most convenient and it gave good results provided the slurry was consistently agitated to prevent the solids settling out. We also tested montmorillonite (bentonite) and kaolinite slurries and observed a change in their appearance after radiation with microwaves. It occurred to us that a mixture of natural zeolite, montmorillonite and kaolinite, irradiated as a water based slurry by microwave radiation, may well produce an enhanced product that may prove more effective for a range of treatments in humans and animals.

In our early experiments we had considerable trouble in keeping the zeolite particles in suspension with the result that often we simply heated the water and did nothing to the zeolite. Also, our stirred batch system was not conducive to continuous production and so we set out to devise equipment for a continuous process. To keep the zeolite particles in suspension during the reaction and subsequently in the finished product we produced stable slurries using bentonite as the stabilising agent. This was a fortuitous choice as we intended to use a blend of zeolite and bentonite with kaolinite considering that this would be likely to have a more beneficial application than zeolite alone. Slurries consisting of 98% zeolite from the Currabubula Formation powdered to a consistency of zeolite having 85% of its particles being less than 76 microns and stabilised with 2% of raw bentonite from the Arumpo Deposit in Victoria, Australia were used for the initial testwork. We also experimented with different radiation times and levels and found that short duration high intensity radiation does not appear to be a substitute for a longer time at a lower radiation level. We concluded that the process will require a finite minimum amount of radiation over a specific minimum time. In our experiments we used 0.09 kW per liter and irradiated for 25 minutes however it is expected that this will be optimised with further experimentation.

The effect of the radiation has not been scientifically defined but it is considered likely that it enhances the loose electron bonds in the crystal structure, thereby increasing its capacity for ion exchange and the absorption of anions, cations and other small charged particles, such as viruses and nano-bacteria. Exactly what else the microwave radiation does to the alumino-silicates is not clear but it is thought that the radiation also disturbs the crystal structure and destabilises some of the silicon atoms making them more readily available for absorbsion by animals being treated with the processed material which, in turn, may well enhance the production of collagen. Work by the Michigan State University has shown that artificial zeolite 'A' provides bio-available silica and enhances collagen production but we can find no evidence of it occurring with natural zeolites.

In order to produce bulk samples for efficacy and economic evaluation tests, a device was developed for continuous processing of the stabilised zeolite slurry. The device consisted of a multiplicity of plastic tubes in a block that forms a continuous fluid passageway that is housed in a microwave proof metal box. The whole system is static and nothing moves except the slurry which is pumped through the tubes at a steady, controlled rate. Several thousand liters of product were made to the formulation of 70% w/w zeolite, 28% w/w kaolinite and 2% w/w bentonite (now named TuffRock) and tested for various applications. These applications include virus and bacteria control, animal condition enhancement, enhanced feed conversion and a poultice for injury recovery.

Empirical Testing

Testwork at various institutions have shown that the above product is very effective for the absorbsion of Roto Virus and *E-Coli*. Empirical field tests have shown that the product cures scour and diarrhoea problems in a range of animals including horses, cattle, pigs, dogs, goats, chickens and kangaroos. Personal tests have shown that it is also effective in humans.

Empirical field tests on healthy animals fed a steady low daily dose of the product have shown an improvement in the animal's wellbeing reflecting as shiny coats, bright eyes and a raised level of alertness and activity. Racehorses and greyhounds fed the product have returned a higher level of wins and placings. The exact reason for this has not been defined but it is thought to be related to a possible higher concentration of bio-available silicon.

Tests on pigs have shown increased feed conversion ratios and increased growth rates. The tests also suggested a reduced incidence of scour although this was not the object of the testwork.

A poultice formulated from the product (by adding to 20 kg of the product 1.5 kg of zeolite and 1.5 kg bentonite to create a paste for topical application) has shown considerably improved recovery rates from wounds, injuries and sores.

Greyhound Puppy Growth Trial

A small scale growth/diarrhoea control study was conducted with 6 greyhound puppies in a greyhound farm called Turbo Park in Hunter Valley, Australia.

Trial Group A

Two greyhounds, one male and one female, were picked at random to be used in the introduction of product into their diet as a liquid supplement added to their nightly dinner, with no other vitamin supplement or electrolyte to be added. The product dosage rate of 1 ml per 10 kg averaged out to 3 ml per greyhound, and the trial lasted 6 weeks.

Control for Trial—Group B

Two more greyhounds were picked out of the litter and these were to be fed the normal feed recipe plus the addition of various vitamin and electrolyte supplements which had proved successful in the past.

Control for Trial—Group C

The remaining two greyhounds were to be fed the normal feed recipe with no supplements to be added at all.

Summary of Results

Group A showed significant improvement compared to the control Groups B and C.

A steady improvement over the 6 weeks was observed in:
Recovery rates and less localised muscle soreness after hard work
Weight Gains—significant in initial stages
Condition of coats, gums, pad texture and nails
Bowel Movements—stools less in volume, harder and with fewer odours
Urine Flow—noticeably lighter in colour and of good flow, even after exercise
Energy Levels—higher and overall nature receptive to pre-training.

Figure 11:
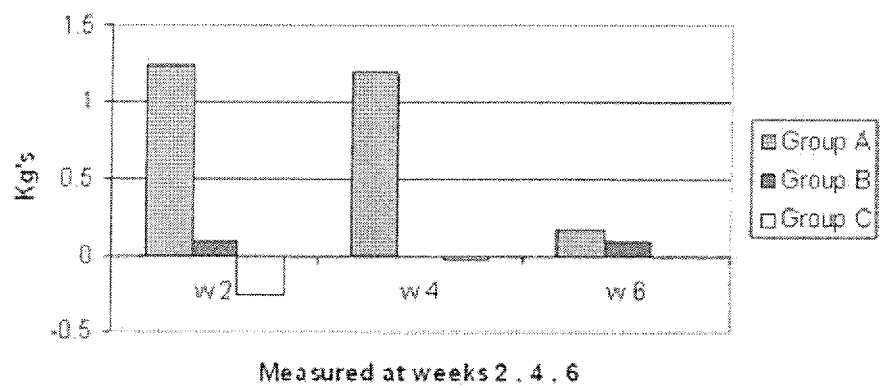
FIG. 11 is a graph of average weekly weight gain measured at weeks 2, 4 and 6 of three groups of greyhound puppies involved in a Greyhound Puppy Growth Trial in which one of the groups was fed product made according to the claimed method of the invention as part of their diet, and the other two groups were fed the normal feed recipe, one of those two groups having vitamin and electrolyte supplements and the other group not having such supplements.

The average weekly weight gain of each of the Groups A, B and C is shown in FIG. 11.

Figure 12:
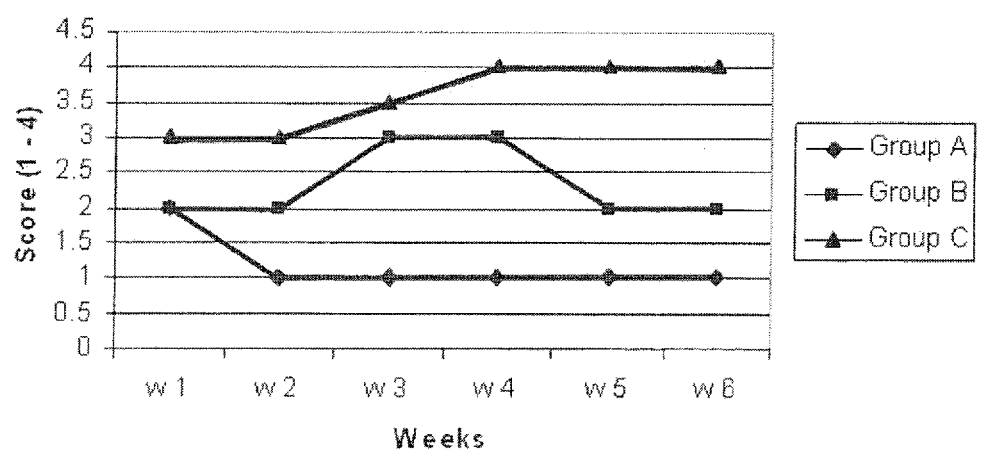
FIG. 12 is a diarrhoea index over 6 weeks of the three groups of greyhound puppies involved in the Greyhound Puppy Growth Trial.
Figure 13:
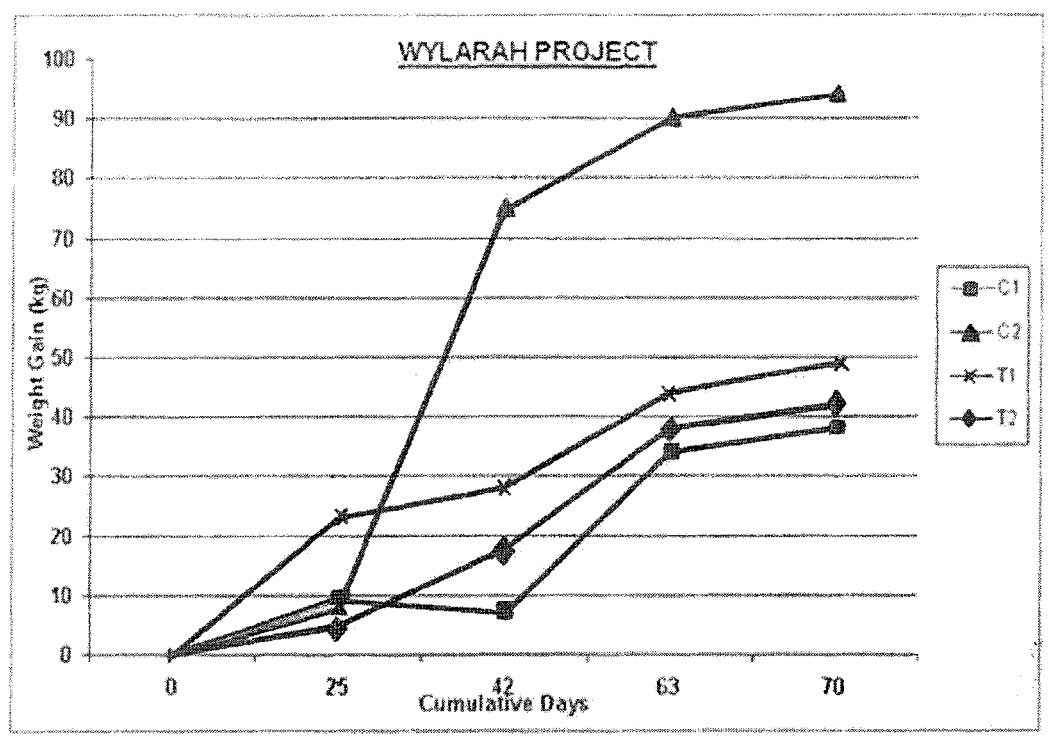
FIG. 13 which is entitled the WYLARAH PROJECT is a graph of Weight Gain over 70 days of four young cattle involved in the trial reported in the example of Case Study 4.

A diarrhoea index of each of the Groups A, B, and C is shown in FIG. 12.

According to the index, an index score of 1 indicates a firm stool, whereas an index of 4 indicates severe diarrhoea.

Conclusions

Although one cannot draw too may conclusions from this study due to small sample size, it still offered very interesting observations:

1. The superiority of Group A puppies performance and their overall condition over Group B and C puppies.

2. The weight gain figures, as shown in FIG. 11, were very impressive (gain of 583 grams per week for Group A puppies compared to gain of 0 g/wk and 0 g/wk) for Group B and C puppies respectively.

3. Whereas puppies in Groups B and C suffered from diarrhoea almost throughout the trial, the puppies in Group A had virtually no diarrhoea, as shown in FIG. 12 (index 1=firm stool, index 4=severe diarrhoea)

4. This trial supports the view that the product according to the invention has a broad spectrum of applications. Whilst piglets are more often affected by bacteria (*E. coli*), the greyhound puppies are often affected by viruses (such as parvo). It appears that the product according to the invention can be effective against both types of pathogens.

Rotavirus Study

One of the most common causes of diarrhoea in foals and piglets is Rotavirus. In addition to being almost impossible to treat, Rotavirus is dangerous because it can result in death of the animal.

An in-vitro trial together with the University of Melbourne was conducted to study the efficacy of the product to bind Rotavirus.

The results were extremely positive as they indicated that the product was capable of binding 98% of the Rotavirus present.

In addition to positive laboratory results, the product has been successful in treating thousands of foals and calves suffering from Rotavirus (at times together with *E. coli*) caused diarrhoea resulting in dramatically reduced recovery times and mortality rates.

Rotavirus Trial of the Product

Method

Serial two fold dilutions of equine Rotavirus (strain 184) in cell culture medium were prepared and equal volumes of the product and each Rotavirus dilution were mixed thoroughly and incubated at room temperature for one hour. After incubation each mixture was centrifuged at 1000 g for 5 minutes to remove the particulate matter from the mixture. The supernatant was removed and the viral RNA was purified by phenol-chloroform extraction. Viral RNA was separated by polyacrylamide gel electrophoresis and stained using silver.

Preliminary Results

The viral nucleic acid was detectable in the 32 fold dilution in the untreated control series, but no viral RNA was detected in the product treated dilution series. This preliminary experiment demonstrated a 32 fold reduction in the amount of virus and strongly indicated that the Rotavirus bound to the product and was removed with the particulate matter.

Clinical Case Report

A cattle property located at "Strathfield" near Manilla in Northern NSW, Australia suffered from a very significant calf scours problem in a herd of 500 Friesian heifers that were mated to a Wagyu bull.

Initially in the calving there were no problems but as the season advanced a large proportion became affected. Testing of faeces samples was undertaken on day 1 and on day 11 to ascertain the cause of the scour. Four calves were sampled on day 1 and the results showed all were positive to *E. coli*, one co-dominant and the others had dense, uniform growth. These *E. coli* were resistant to Sulphonamides, tetracyclines and ampicillin. One of the samples was positive to Rotavirus. Two further samples were taken on day 11 and they were positive to *E. coli* and Rotavirus respectively. Two post mortems were also undertaken on day 12, and these revealed multisystemic organ failure most likely due to dehydration and septicaemia. *E. coli* was found in dense growth in the bowel and this was resistant to all drugs tested with (neomycin and trimethoprim sulphonamides, as well as the drugs identified above).

Treatment of these animals consisted of the use of oral electrolytes for re-hydration (commercially available Vytrate™, Diarrest™ and ResQ™ electrolyte preparations were used), and antibiotics including neomycin, timethoprim sulfonamide and oxytetracycline were used to treat bacterial pathogens and guard against septicaemia. Animals showing signs of pneumonia were treated with ceftiofur. Severely pyrexic animals were given flunixin if their dehydration was not severe and improving. Initially scourban was used as well; this was replaced by the product of the present invention later in the study.

The infection on this property was severe, and of the first 250 heifers to calve it was estimated that 70% of the offspring suffered scours. There were 42 deaths in these calves, and it was after this point that the product was used on the remaining calves. The initial dose used was approximately 1.5 times the labelled dose of 1 ml of product/kg weight animal, with a maximum of 100 ml per dose for each calf. Treatment was repeated at 12 hours if the calf had deteriorated and at 24 hours if scouring was still severe. Calves were then reassessed every 12 hours as to their need for re-treatment. Most animals required only 2 treatments with the product, and the maximum was 5. The product was used as the first treatment and was followed by electrolytes approximately 30 minutes later.

Following the early introduction of the product into the treatment regime, there was a significant reduction in the mortality rate, with only four more calves dying. Only a further 100 calves were born on the property before the heifers were moved to other properties for calving to reduce their exposure to the pathogens. Of these it was estimated that 90% suffered from scours. It was observed that the product significantly reduced ongoing fluid losses from the calves, and reduced the average time that the calves were off their mothers back from approximately 4 days to 3.

Discussion

The natural absorbent properties of the product of the present invention are ideal to normalize bowel function after an acute diarrhoea episode. The product provides both a coating and absorbent action, minimizing further fluid loss, with natural ingredients, thereby achieving a clinical improvement without sustained pharmaceutical therapy.

The product has proved useful in both the primary management of non-specific acute diarrhoea and as adjunctive therapy during the recovery phase of acute viral/bacterial infectious episodes. The discussion that follows relates, for purposes of example only, to the treatment of dogs.

Acute Diarrhoea—Primary Therapy

Dogs presented for examination and treatment which were bright and happy, afebrile (with no elevated temperature) and had no vomiting needed investigation to eliminate the possible simple causes of diarrhoea. Specifically, a faecal examination is the first place to start to determine the possible presence of parasites whilst obtaining a thorough recent history to assess access to gut irritants or toxins. If no likely cause is discernable, symptomatic treatment, without antibiotics, is a valid course of action for primary therapy in the young to middle aged dog.

The product of the present invention is ideally suited as a gentle natural absorbent and detoxifier with protective and intestinal coating actions which will help normalize digestive physiology. Two to four doses 12 hourly at the dose rate of 1 ml per kg body weight will usually resolve such diarrhoea within 48 hours.

Acute Viral Diarrhoea—Adjunctive Therapy

In acute attacks of Corona-virus, parvovirus, haemorrhagic gastroenteritis, febrile gastroenteritis, clinical improvement is first necessary with fluid therapy and therapeutic management to control temperature and vomiting, followed critically by treatment with absorbents and intestinal protectants.

Oral administration of the product following control of animal temperature and vomiting helps to normalize bowel function naturally, and the need for prolonged antimicrobial therapy is reduced and recovery times shortened.

Chronic Diarrhoea—Dietary Sensitivities

Chronic cases of persistent or episodic diarrhoea require investigation to determine a likely cause. Specific therapies may be indicated by such investigation including management for exocrine pancreatic insufficiency, malabsorption syndrome, parasites, food intolerance or food allergy. At times a definitive diagnosis may be difficult, particularly in the case of food intolerance.

Toxins and secondary fermentation from incompletely digested dietary components often contribute to this clinical condition. Gluten intolerance has been implicated in many cases in dogs on a high dry food component diet.

The product of the present invention has been specifically formulated to promote toxin absorption, reduce fermentation and promote a more normal digestive physiology in those cases of low grade digestive irritability.

A general clinical improvement has been observed after treatment with the product in those individuals eating pet meat with known preservative content. This often is implicated in irregular bowel motion consistency, particularly in summer, and the product has been effective in such cases.

Case Study 1

Clinical Experiences with TuffRock

Preamble

TuffRock products have been trialled extensively in many species however this document refers to my clinical experiences in the dog. The same principles of action apply and species cross-extrapolation only requires dose determination.

The familiar problem of promoting a nutraceutical that exerts a highly efficacious therapeutic action, provides a particular situation that needs to be addressed with each Veterinarian in such a way so as to not directly make any therapeutic claims, yet to convey efficacy so as to engender confidence to "get the product into the clinic". Once tried the value of such a product will be evident and its "NATURAL" connotation will make it an easy product to dispense with the general public's perception that those things "Natural" are "Good".

[A similar situation was faced with "Sasha's Blend" wherein direct therapeutic claims could not be made, however its "Natural" slant and simplistic efficacy has given it a large market share as protective and adjunctive therapy.]

Petit Plus & Canine Conditioner

Petit Plus and Canine Conditioner are forms of TuffRock, the product of the present invention.

The Natural absorbent properties of Petit Plus are ideal to normalize bowel function after an acute diarrhoea episode. It provides both a coating and absorbent action, minimizing further fluid loss, with natural ingredients, thereby achieving a clinical improvement without sustained pharmaceutical therapy.

Petit Plus has proved useful in both the primary management of non-specific diarrhoea and as adjunctive therapy during the recovery phase of acute viral/bacterial infectious episodes.

Acute Diarrhoea—Primary Therapy

Dogs presented at the Hospital bright & happy, afebrile (with no elevated temperature) and with no vomiting need investigation to eliminate the possible simple causes of diarrhoea. Specifically a faecal examination is the first place to start to determine the possible presence of parasites whilst obtaining a thorough recent history to assess access to gut irritants or toxins. If no likely cause is discernable symptomatic treatment, without antibiotics, is a valid course of action for primary therapy in the young to middle aged dog.

Petit Plus is ideally suited as a gentle natural absorbent, detoxifier with protective and intestinal coating actions which will help normalize digestive physiology. Two to four doses 12 hourly at the dose rate of 1 ml per kg, bodyweight will usually resolve such diarrhoea within 48 hours.

Acute Viral Diarrhoea—Adjunctive Therapy

Acute cases of Corona-virus, parvovirus, haemorrhagic gastroenteritis, febrile gastroenteritis—once clinical improvement is achieved with fluid therapy and therapeutic management as indicated to control temperature and vomiting then absorbents and intestinal protectants are of critical importance.

Petit Plus administered orally achieves this and helps to normalize bowel function naturally, and the need for prolonged antimicrobial therapy is reduced and recovery times shortened. It is a useful adjunctive therapy for hospitalized patients prior to discharge as well as to dispense as part of initial home therapy.

Chronic Diarrhoea—Dietary Sensitivities

Chronic cases of persistent or episodic soft motions require investigations to determine a likely cause. Specific therapies may be indicated by such investigations including management for exocrine pancreatic insufficiency, malabsorption syndrome, parasites, food intolerance or food allergy. At times a definitive diagnosis may be difficult, particularly in the case of food intolerance.

Toxins and secondary fermentation from incompletely digested dietary components often contribute to this clinical entity. A gluten intolerance has been implicated in many cases in dogs on a high dry food component diet.

TuffRock Canine Conditioner has been specifically formulated to promote toxin absorption, reduce fermentation and promote a more normal digestive physiology in those cases of low grade digestive irritability.

A general clinical improvement has been observed after Canine Conditioner in those individuals eating pet meat with known preservative content. This often is implicated in irregular bowel motion consistency, particularly in summer, and Canine Conditioner Plus has been effective in such cases. The preservative treated meat is not reserved for greyhound consumption only.

Case Study by Dr John Newell B. V. Sc.

Case Study 2

Foal Plus & Conditioner—"MAC"—Cushings Disease Case Study

Duration 8 weeks ending AUGUST 2006, Location: Wagga Wagga, Australia

"Cushings Kit"—1 carton of Tuffrock containing 6 liters of Foal Plus and 3 liters of Conditioner. Foal Plus and Conditioner are forms of TuffRock, the product of the present invention Riding for the Disabled Association (NSW) is a large charity organisation that provides equine assisted activities for people with disabilities. At Wagga centre we are lucky to be donated a variety of horses to use in our programs, many of whom are aged and in sub-optimal condition when they arrive at our centre. 'Mac' is one such pony that has been with us for several years.

In his mid-twenties, Mac is a favourite amongst our younger riders, not only because of his lovely nature, but also because of his long curly white coat. Mac often resembles an angora goat due to a condition known as 'Cushing's Disease'. Since he is such a favourite, (and so white!) it is very distressing to all in contact with Mac when he suffers from 'the scours' each winter.

Whilst we have tried many management strategies to reduce Mac's scouring and consequent weight loss, not much seemed to work. It was after hearing about TuffRock's products, and seeing the effectiveness of "Conditioner Plus" in some of our geriatric horses that we decided to try "Foal Plus" on Mac.

Results achieved by orally administering 'Foal Plus' twice daily, application rates:

| Day number | Morning (mls) | Evening (mls) | Cumulative (mls) |
| --- | --- | --- | --- |
| 1 | 200 | 200 | 400 |
| 2 | 175 | 175 | 750 |
| 3 | 150 | 150 | 1050 |
| 4 | 12S | 125 | 1300 |
| 5 | 125 | 125 | 1550 |
| 6 | 125 | 125 | 1800 |
| 7 | 100 | 100 | 2000 |
| 8-27 | 100 | 100 | 6000 for effect |

Mac then went on to a daily maintenance dose of Conditioner Plus 20 ml (1 Tablespoon)

After 4 weeks of treatment Mac's diarrhoea has nearly ceased.

Whilst there is some residual staining (Mac was not washed during the treatment) there is only minimal diarrhoea present.

Mac's condition improved greatly over the 4 weeks, and I am happy to report that he now has 'solid' manure, and no 'yucky legs' as one of our riders described it!

Mac loves the TuffRock taste and really enjoys the daily tablespoon of Conditioner Plus in his feed.

Being a student nearing completion of a Bachelor of Applied Science (Equine) Degree, I must admit that I was sceptical of this treatment initially, but having seen first hand the results we obtained using TuffRock Foal Plus and following with Conditioner Plus I would recommend use of these products on horses similar to Mac.

Not only has his scouring ceased, but he is brighter within himself and is able to make better use of his feed and is now putting on some condition, allowing him to continue the valuable job he performs and brightening the day of our special riders.

The simplest way I tell people about this amazing result is to describe this as a "Cushings Kit". One carton of TuffRock containing 6 liters of Foal Plus and 3 liters of Conditioner and try it for yourself.

Michelle Eastwood (Final Year) Bachelor of Applied Science (Equine) Degree, Charles Sturt University Case Study complied for Rob Lidgard (Manager), RDA (NSW), Wagga Wagga Centre, AUSTRALIA.

Case Study 3

It has been found that a small daily dose of TuffRock improves the metabolism of animals in poor condition and restores them to good health. In the absence of any practical parameter that could be measured, the most efficient way of assessing the efficacy of TuffRock in this role is by observation and visual assessment by an expert in this field.

Figure 2:
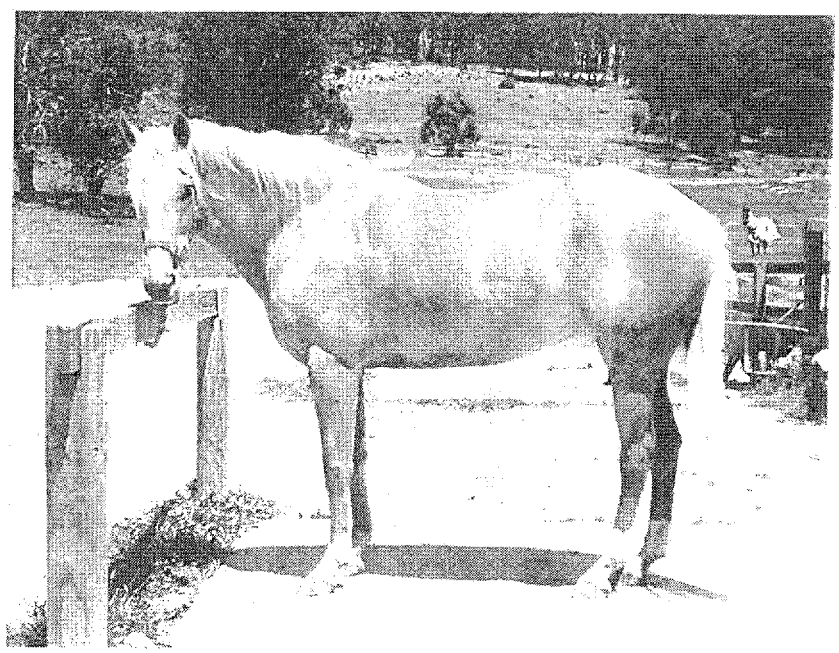
FIG. 2 is a photograph of the horse taken after 14 weeks of the aforementioned trial.

A test was set up on a property in the Southern Highlands of New South Wales, Australia, which is owned by Ms Kate Fenner who is an expert trainer of horses. The animal chosen was in very poor condition (see FIG. 1) and had several other problems. The horse was fed a daily dose of 20 milliliters of TuffRock per day dispersed in a small quantity of a mixture of bran and pollard to help with administering such a small quantity of liquid (designated TuffRock Conditioner for the trial). At the beginning of the trial the horse was thin, listless, disinterested, had a dull poor coat and laid back ears. After 14 weeks of treatment the horse had gained weight, was alert, interested in its surroundings, had a bright shiny coat and erect ears (see FIG. 2). It was also reported that appetite was considerably improved and that it had largely overcome a windsucking problem. Kate Fenner's findings are reported below.

"Beauleigh Showtime, Nugget, is a 7 year old Australian Stock Horse mare. At the time of the first picture (FIG. 1) she had just been brought in from the paddock having spent 6 months recovering from a shoulder injury. She is a chronic windsucker and a very fussy eater. I put Nugget on "TuffRock Conditioner with Calcium" and found her appetite increased hugely. In my opinion, this in turn led to a substantial reduction in the windsucking. Her coat improved enormously and the TuffRock Conditioner does not cause 'smutting', which is important in the Palomino colouring."

Kate Fenner—KANDOO EQUINE—www.kandooequine.com.au

Case Study 4

Several empirical tests have indicated that a daily dose of TuffRock improves weight conversion in animals. In order to show that the administration of TuffRock to calves over their growing out period improved their rate of weight gain the following trial was organized.

Efficacy Testing of "TuffRock CCC"

1. Background

TuffRock Pty Limited has developed a range of natural mineral products for the Animal Husbandry Industry. One of these products is Cattle Conditioner plus Calcium ("CCC") and which has been developed to increase the feed conversion of calves and young cattle and thereby improve the efficiency of feedlots and of open range cattle farming. In order to show that the product is technically effective, an initial trial was set up with Wylarah Pastoral Company in the Southern Highlands of New South Wales, Australia.

2. TuffRock Cattle Conditioner Plus Calcium

Several previous empirical tests on pigs and other animals have indicated that our "TuffRock" processed liquid product has the ability to improve feed conversion and to increase weight gain. This new product is essentially our TuffRock liquid blended into pollard and bran with a small amount of calcium additive. The function of the bran and pollard is to allow the minute quantities of TuffRock required to be better distributed in the feed. Because of the nature of bran and pollard and the very small quantity fed to the animals, it has almost no nutritional value and therefore any effect this product has on animals is due to the TuffRock liquid contained in the mix. TuffRock CCC is a feed additive and has little or no nutritional value.

3. Test Environment

Figure 3:
FIG. 3 is a photograph of one side of the divided test paddock used in the trial reported in the example of Case Study 4.
Figure 4:
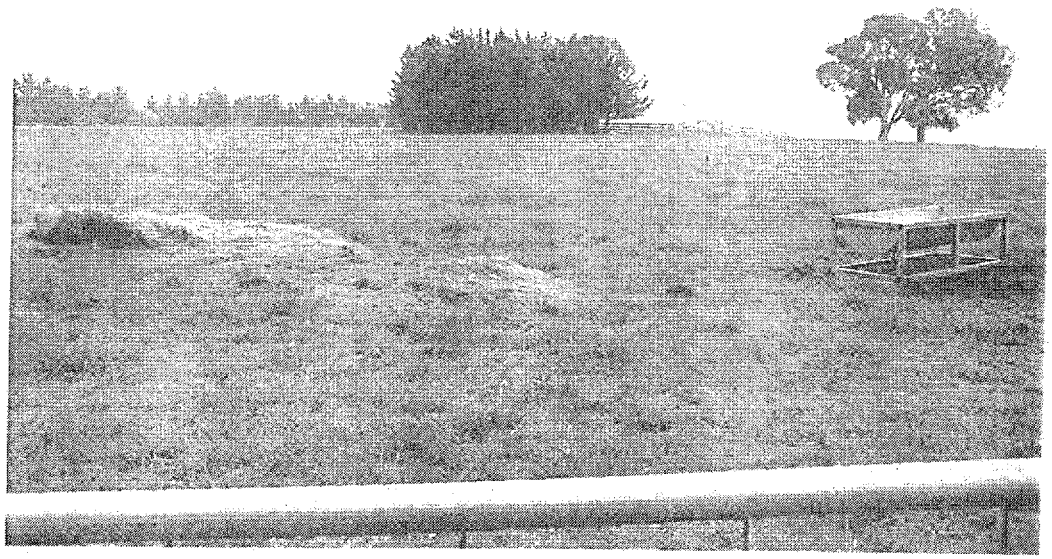
FIG. 4 is a photograph of the other side of the divided test paddock used in the aforementioned trial.
Figure 5:
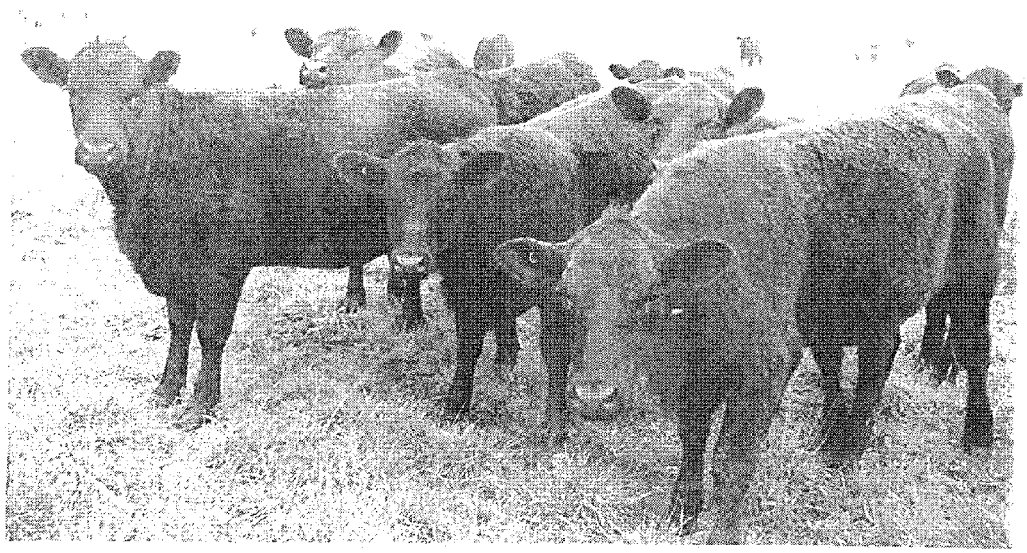
FIG. 5 is a photograph of Angus cattle similar to those used in the aforementioned trial.
Figure 6:
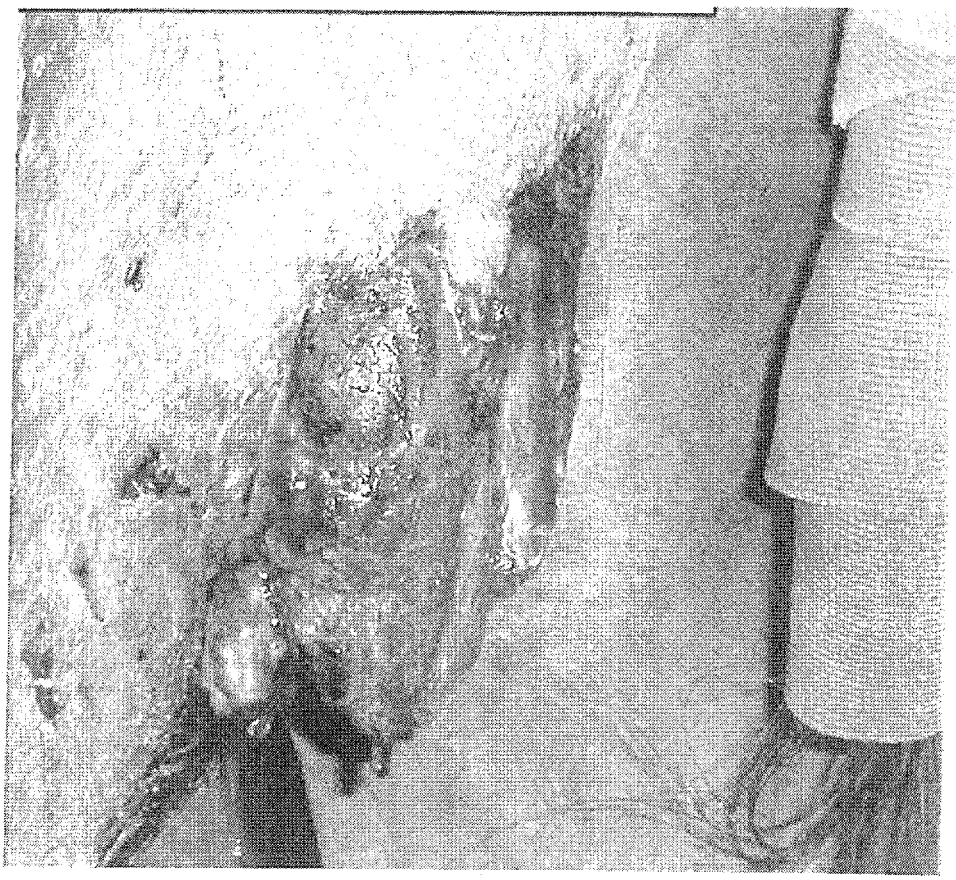
FIG. 6 is a photograph of the initial injury or wound (bottom entry) of the horse involved in Case Study 5.
Figure 7:
FIG. 7 is a photograph of the initial wound (top exit) of the horse involved in Case Study 5.
Figure 8:
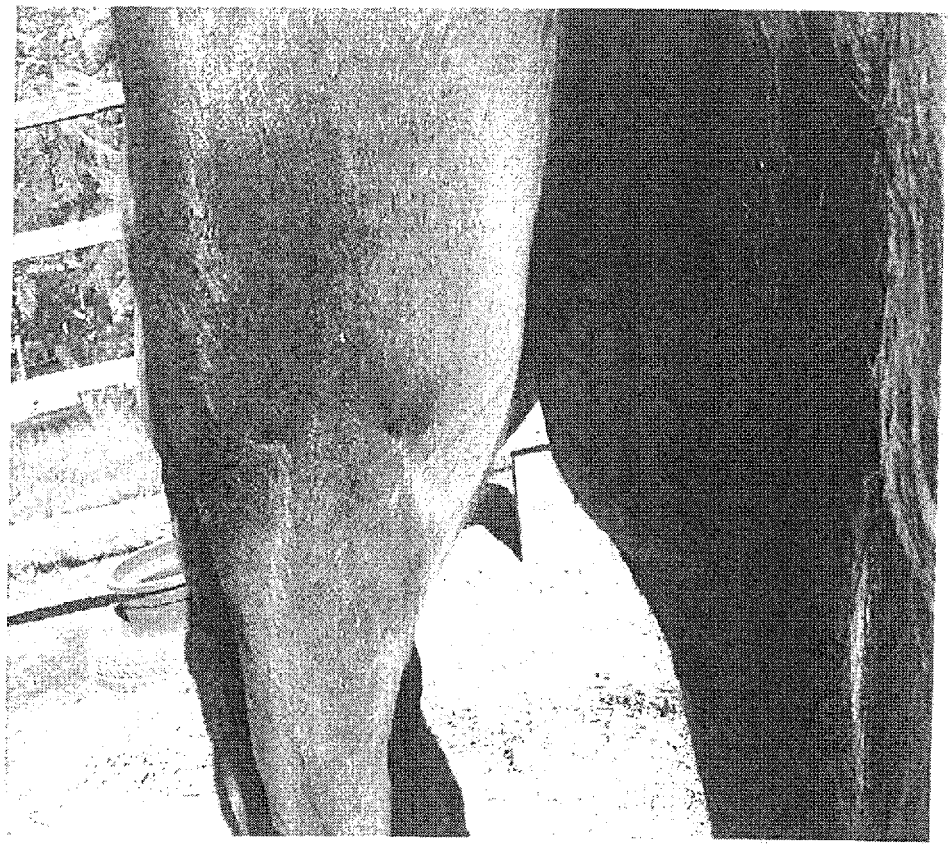
FIG. 8 is a photograph of the wound (bottom entry) of the horse at the end of Case Study 5.
Figure 9:
FIG. 9 is a photograph of the wound (top exit) of the horse at the end of Case Study 5.
Figure 10:
FIG. 10 is a photograph of the horse taken after six weeks of the aforementioned Case Study.

Wylarah might best be described as a Natural Feedlot whereby cattle are bred and grown out in small, carefully controlled paddocks. They feed on natural grass but are also fed silage, hay and pellets as required, depending on the availability of natural feed. For this test a paddock was divided into two equal portions with respect to area and available grass. A common water trough on either side of the dividing fence line was provided and separate feed troughs were also provided in each equal portion of the paddock. FIG. 3 shows one portion of the divided test paddock, and FIG. 4 shows the other portion of the paddock. All cattle were fed exactly the same feed except that the "TuffRock" cows were also fed 50 grams per day per animal of "TuffRock CCC". Our recommended adequate dose rate is 0.1 grams per kilo body weight per day, which would average 25 grams per animal per day for the test animals. However, excess dosage is not detrimental and the optimum dosage rate is simply a matter of economics. The breed of cows used was Angus (see FIG. 5). It was initially intended that the test be conducted in summer when there was an abundance of grass and that 10 cows divided into two equal groups of 5 would be used. For various reasons the test was delayed to mid-winter and a total of only four cows were available for the test.

As the test was conducted in mid-winter, the weather was cold to very cold and available grass became somewhat restricted during the test. The animals were fed one bail of straw and one bail of high class silage per day to augment their feed. To help distribute the TuffRock CCC in their feed trough they were also fed 1.5% of body weight of Lucerne chaff and after 14 days into the test some additional "14% protein" pellets were also provided. From the start of the fifth week (after 35 days) they were fed an excess of pellets to ensure that they had enough feed. Cows C1 and C2 are the control cows and cows T1 and T2 are the TuffRock test cows. All cows were weighed at regular intervals.

4. Results

Control cow C2 showed abnormal results. For the first 25 days it showed a normal weight gain of some 0.36 Kg/day. Over the next 17 days it showed a weight gain of 3.94 Kg/day which seems abnormal and not representative of normal behavior (refer to the slope of the curve in Table 4). From day 42 to the end of the test the weight gain for this cow is again relatively normal (refer to the slope of the curve in Table 4). The results for this cow are not considered to be representative and have therefore been discounted from the results (see Table 3).

Of the results, only Cow C1 and Cows T1 and T2 can therefore be used to draw a comparison. The results show that there is an improvement in weight gain using TuffRock CCC for the first 63 days and after that the rate of weight gain is similar with or without TuffRock.

Visual observation showed that the cows on TuffRock were less fussy in their eating habits than the control cows and that they would readily eat the poorer quality feed.

The results show that the feeding of TuffRock CCC for the first 8 to 9 weeks results in an additional weight gain and that after that the rate of weight gain is relatively equal for animals with or without TuffRock CCC. For the test the TuffRock cows showed an additional weight gain of some 20% over the control cows.

TABLE 1

WYLARAH PROJECT

| | DATE | | | | | Av. Kg/ | % |
| | May 26, 2010 | Jun. 21, 2010 | Jul. 8, 2010 | Jul. 30, 2010 | Aug. 6, 2010 | Kg/day | day | Increase |
|---|---|---|---|---|---|---|---|---|
| DAYS | 0 | 25 | 17 | 21 | 7 | | | |
| DAYS CUM. | 0 | 25 | 42 | 63 | 70 | | | |
| | | | Total Weight (Kg) | | | | | |
| CONTROL 1 | 267 | 276 | 274 | 301 | 305 | | | |
| CONTROL 2 | 221 | 229 | 296 | 311 | 315 | | | |
| TUFFROCK 1 | 267 | 290 | 295 | 311 | 316 | | | |
| TUFFROCK 2 | 242 | 247 | 260 | 280 | 284 | | | |
| | | | Weight Gain (Kg) | | | | | |

TABLE 1-continued

WYLARAH PROJECT

| | DATE | | | | | Av. Kg/ | % |
|---|---|---|---|---|---|---|---|
| | May 26, 2010 | Jun. 21, 2010 | Jul. 8, 2010 | Jul. 30, 2010 | Aug. 6, 2010 | Kg/day | day | Increase |
| DAYS CUM. | 0 | 25 | 42 | 63 | 70 | | | |
| CONTROL 1 | 0 | 9 | 7 | 34 | 38 | 0.543 | 0.5429 | |
| CONTROL 2 | 0 | 8 | 75 | 90 | 94 | 1.343 | | |
| TUFFROCK 1 | 0 | 23 | 28 | 44 | 49 | 0.700 | | |
| TUFFROCK 2 | 0 | 5 | 18 | 38 | 42 | 0.600} | 0.6500 | 120% |

5. Conclusion

Although the test sample was too small and the weather conditions less than ideal, the test nonetheless indicated that TuffRock CCC is effective in improving feed conversion of cattle which results in an overall weight gain.

Case Study 5

It is postulated that the radiation applied to make "TuffRock" may well partially disrupt the crystal lattice of the alumino-silicate minerals, resulting in the release of some silicon atoms. These nascent silicon atoms are in turn expected to be bio-available to an animal, resulting in the generation of collagen and therefore rapid healing of wounds. Empirical tests using TuffRock liquid indicated rapid healing of wounds with very little scarring. In order to test the efficacy of TuffRock for this purpose a Poultice was made by blending TuffRock liquid into a relatively inert carrier to a paste consistency. A test was set up on a seriously injured horse (named Nookie) and as there are no physical parameters that can reasonably be measured for this type of test, an extensive photo record was kept and the progress of the healing process observed. The details of the animal and the record of the treatment procedure are as follows:

- Nookie, a Quarter horse gelding 14.5 hands, reigning horse, for unknown reasons decided to go through a fence and sit on a steel star picket stake. The steel stake entered the lower leg and protruded up through the upper buttock.
- Top wound (stake exit) was nominally 230 millimeters down and 150 millimeters across with 10 stitches.
- Bottom wound (stake entry) was nominally 150 millimeters diameter with 250 millimeters of muscle protruding.
- The animal was hospitalized with the vet for 1 week then returned to owner's stable.
- The Vet's recommendation was to regularly clean the wound with a hose, to use septicide on wound to keep flies away and to fight infection in combination with oral sulphur paste.
- No antibiotics were given to horse by the owner, septicide was stopped after 24 hours and TuffRock was introduced to the protocol. Sulphur paste was continued for the initial 3 weeks and then stopped.
- TuffRock Conditioner was added to the diet at a rate of 20 ml twice a day with feed to help with the animal's general condition.
- TuffRock Poultice was applied like putty, filling holes and used on any hot spots or swollen areas. This was done twice daily for 6 weeks with the wound exposed to air for 15 minutes in between each application.
- TuffRock Poultice was removed wet for first 4 weeks until the pus stopped.
- TuffRock Poultice was then removed dry for last 2 weeks.
- Leg wounds, including superficial lacerations and deeper scratches, and leg swelling were fixed with only 2-3 days of TuffRock application.
- Horse was kept inside stable first 2 weeks then yarded.
- Poultice kept flies away.
- No proud flesh.
- No additional surgery required apart from the removal of stitches.
- Wound heal time was very rapid, being only 6 weeks.
- Visual evidence shows no scar on entry wound and complete skin re-growth, with a minor exit wound scar where the stitches were.

The photographs in FIGS. 6 to 10 show the initial injury and the final result after 6 weeks of treatment.

Case Study 6

The Effect of TuffRock in Diets for Weaned Piglets

A 32-day growth performance experiment was carried out with a total of 96 weaned piglets from 16 litters to study the effect of adding increasing levels (0, 0.3 or 0.6%) of the volcanic earth product TuffRock, which is a mixture of aluminosilicates, kaolin, halloysite and bentonites, in weaner diets on piglets' growth performance, feed utilisation and the incidence of post-weaning diarrhoea. The piglets were weaned in the average age of 27.2 days, and then their mean body weight was 9.3±1.0 kg. The piglets were housed in pairs and were given ad libitum pelleted diets (Ø2.5 mm) with high energy and nutrient density (10.0 MJ NE and 10 g apparent ileal digestible lysine per kg feed). The isoenergetic and isonitrogenous diets consisted of wheat, barley, soybean meal, soyprotein concentrate, whey protein concentrate, rapeseed oil, pure amino acids, and mineral and vitamin supplements. Dietary pH was 5.65, 5.67 and 5.67 in diets with 0, 0.3 and 0.6% Tuff Rock, respectively. Although TuffRock contains sodium bentonite, which can act as a binder in the pelleting process, the largest TuffRock addition reduced slightly both the durability and hardness of pellets. This could have been caused by increased amounts of added fat in TuffRock diets.

Increased dietary TuffRock additions resulted in positive effects on piglets' weight gain and feed consumption during the 32-day experimental period. These effects were the profoundest during the first 2-3 weeks after weaning. During the whole 32-day experiment, dietary Tuffrock additions had a quadratic effect on piglets' weight gain and feed conversion ratio. The best growth performance was seen in piglets that received the diet containing 0.6% TuffRock. In the end of the experiment, these piglets were the heaviest and had consumed the largest amount of feed. Feed conversion ratio was the poorest in piglets fed the diet with 0.3% TuffRock, while that of piglets receiving 0.6% TuffRock in their diet did not differ from the control.

Diarrhoea was observed in 48% of the pens, while softened faeces or no diarrhoea were seen in 17% and 35% of the pens, respectively. The piglets begun to scour 5-6 days after weaning with scouring peaking 8-12 days after weaning. Faecal consistency returned to normal within 3 weeks after weaning. There were no significant differences between the treatments in the number of diarrhoea days or in the severity of diarrhoea which was measured as diarrhoea index (sum of daily diarrhoea scores). Numerically the number of diarrhoea days and diarrhoea index decreased slightly with increased dietary TuffRock additions and the number of pens with severe diarrhoea was the smallest when the weaner diet was supplemented with 0.6% TuffRock. The patterns of daily mean diarrhoea scores showed slight reduction in the severity and duration of post-weaning diarrhoea in piglets fed TuffRock diets.

The frequency of gastric alterations was generally high and could have been related to the diet composition (plenty of wheat and whey protein concentrate) and/or pelleting. The pH difference between the proximal and distal stomach contents became smaller with increasing dietary TuffRock additions. A slight, although not significant increase in the severity of gastric lesions in the pars oesophageal area could indicate an increased risk for gastric ulcers in TuffRock supplemented diets. However, the reason for this remained unclear.

Case Study 7
The Effect of TuffRock on Broiler Chickens

TuffRock is a blend of volcanic minerals that are selected based on their intrinsic geological age and absorption and binding capabilities. The ingredients are refined and molecularly reinforced to improve their absorption capabilities and then blended into TuffRock paste. Primary Ingredients are a blend of energised (electric charged) volcanic sodium, potassium and calcium alumino-silicates.

TuffRock has been shown to bind to pathogenic bacteria, viruses and protozoa. This action is created by positive and negative charges which attract each other to form a bond. Pathogens are attracted to the molecular charged TuffRock, and are then locked inside the 3-dimensional crystalline structure and naturally removed with faecal matter. Laboratory tests have also shown this material to bind with particular toxins and gasses, especially ammonia.

Effects of TuffRock on performance and health status of growing broiler chickens are reported herein. Improvements in performance and health of the broilers could be especially evident when no coccidiostats are fed and environmental microbial challenge is high. The objective of this trial was to study the effect of TuffRock animal feed additive on performance, feed conversion ratio and health of broilers and to investigate mode of action of TuffRock in the gastrointestinal tract of chickens.

A total of 3072 "Ross 508" broiler chickens (each being 1 day old) were obtained from a hatchery. They received experimental diets from day 1 to day 38 and the temperature and light were controlled according to Ross broiler breeder instructions. The experimental design was the dietary inclusion of TuffRock animal feed additive (0, 0.8 or 4.0% of Tuffrock). Six treatments were fed to 8 replicates. Pens were randomly allocated to the dietary treatments.

The six treatments were:
1. Coccidial vaccination and TuffRock 0% (control)
2. Coccidial vaccination and TuffRock 0.8% (normal feeding level)
3. Coccidial vaccination and TuffRock 4.0% (toxic feeding level)
4. Coccidiostat and TuffRock 0% (control)
5. Coccidiostat and TuffRock 0.8% (normal feeding level)
6. Coccidiostat and TuffRock 4.0% (toxic feeding level)

The experimental diets were typical European broiler diets and were formulated to meet the nutrient recommendations of Ross breeder management guide. The diets contained 0, 0.8 or 4.0% of TuffRock feed additive. Coccidiostat was added to half of the diets (treatments 4, 5 and 6). Half of the broilers received anticoccidial vaccination sprayed in their starter feed in the beginning of the trial (treatments 1, 2 and 3). Feeding and water were offered ad libitum throughout the study. Animal health was monitored daily. Dead animals were weighed and removed. Birds were weighed at the beginning, at 7 and 21 days of age, and at the end of the experiment (38 days of age) by pen. The carcass weight of each pen was measured at day 39.

Samples were taken from the litter at 21 days of age and at the end of the experiment and analysed for dry matter content. The litter samples from day 21 were analysed for the number of Eimeria oocysts, as well. Three broilers from each pen were randomly selected at day 21 for intestinal sampling.

The broilers in all treatments grew well without any clinical signs of sickness or toxicity. The coccidiosis control method had the greatest effect on body weight and growth of the broilers. Coccidial vaccinated birds were smaller and grew slower during the whole trial.

TuffRock feed additive increased body weight and growth of the broilers during the first 21 days. The body weight of the broilers tended to be greater on day 7 and was greater on day 21 with dietary TuffRock supplementation. Feed intake of the coccidial vaccinated broilers was lower than that of the broilers fed coccidiostat during the first week of the trial. Coccidiosis treatment had no effects on the feed intake during the rest of the periods of entire trial. Dietary coccidiostat improved feed conversion rate (FCR) of the broilers between days 7 and 21 and during the whole trial. Moreover, dietary coccidiostat improved feed conversion per carcass weight during the entire trial.

TuffRock supplementation increased the feed intake of the broilers during every feeding compared to control diets with no TuffRock supplementation. There was significant interaction between the coccidiosis treatment and TuffRock supplementation in the feed intake. The feed intake of the broilers fed 4.0% TuffRock with coccidiostat increased especially during the later part of the trial (between days 22 and 38). TuffRock supplementation (treatments 2, 3 and 6) increased the feed intake of the broilers between days 8 and 21 compared to the control treatment (treatment 1). In addition, feed intake of the broilers fed highest TuffRock supply with dietary coccidiostat (treatment 6) was higher than that of the broilers fed the other treatments during the last two and a half weeks of the trial. During the whole trial, TuffRock supplementations (treatments 2, 5 and 6) enhanced feed intake of the broilers compared to the control treatment (treatment 4). In addition, the total feed intake of the broilers fed treatment 1 was lower than that of the broilers fed treatment 6.

No differences were observed in FCR during the first week of the trial. Dietary coccidiostat (treatments 4, 5 and 6) improved FCR of the broilers compared to coccidial vaccination (treatments 1, 2 and 3) between days 8 and 21 and during the whole trial.

Dietary TuffRock decreased the mortality of the broilers during the first week of the trial especially when the treatments contained no dietary coccidiostat. In general, TuffRock supplementations decreased the mortality of the broilers during the entire trial period.

During the first three trial weeks, TuffRock supplementation increased the body weight gain of the broilers but had no effects on the feed conversion rate. In addition, TuffRock supplementation decreased the mortality of the broilers during the first trial week especially in treatments with coccidial vaccination. TuffRock increased pH and decreased volatile fatty acid content of ileal digesta in samples taken on day 21. This observation indicates that TuffRock has antimicrobial effect in the small intestine and could explain increased growth and decreased mortality.

During the entire trial, TuffRock had no effects on the growth of the broilers. TuffRock increased the feed intake of the broilers and therefore impaired feed conversion rate especially during the last two and a half weeks of the trial (between days 22 and 38). However, TuffRock supply had no effects on the feed intake per carcass weight gain. Increased feed intake indicated lower metabolic energy value of the TuffRock diets.

TuffRock supplementation decreased the mortality of the broilers during the entire trial, as well. This observation gives further evidence of antimicrobial effects of TuffRock.

TuffRock supply, at a low or high level, caused no clinical signs of toxicity or sickness to the birds.

Coccidial vaccination impaired the performance of the broilers especially during the first three weeks of the trial. In addition, coccidial vaccination increased the mortality of the birds during the first week of the trial. TuffRock and coccidial treatment had no clear interaction.

It will be apparent to persons skilled in the art that various modifications may be made in details of composition of the natural alumino-silicate minerals having improved reactivity, and in details of the process for producing same and the method of treatment with same, without departing from the scope or ambit of the invention.

The invention claimed is:

1. A method of treating digestive ailments in non-human animals comprising administering to a non-human animal in need of same an effective amount of a composition comprising natural alumino-silicate minerals which have been irradiated with transverse electromagnetic wave radiation in the range of 1,800 MHz to 3,000 MHz to increase the electric charge of the alumina-silicate minerals sufficiently for them to absorb small charged particles which cause the digestive ailments wherein the natural alumina-silicate minerals comprise 70% w/w zeolite, 28% w/w kaolinite, and 2% w/w bentonite, wherein the transverse electromagnetic wave radiation has an intensity of about 0.09 Kw per liter of the composition and is applied for about 25 minutes.

2. The method of claim 1 wherein the natural zeolite minerals are selected from the group consisting of clinoptilolite, mordenite, chabazite, erionite and stellerite.

3. The method of claim 1, wherein the composition is a water-based suspension.

* * * * *